United States Patent [19]
Lu

[11] Patent Number: 5,925,067
[45] Date of Patent: Jul. 20, 1999

[54] AUTOMATIC CAPTURE DETECTION DURING NON-INVASIVE PROGRAMMED STIMULATION OF A PATIENT'S HEART

[75] Inventor: Richard Lu, Thousand Oaks, Calif.

[73] Assignee: Pacesetter, Inc., Sylmar, Calif.

[21] Appl. No.: 08/988,582

[22] Filed: Dec. 11, 1997

[51] Int. Cl.⁶ ................................................. A61N 1/362
[52] U.S. Cl. ............................................. 607/28; 607/27
[58] Field of Search .................................. 607/17, 27, 28

[56] References Cited

U.S. PATENT DOCUMENTS

| | | | |
|---|---|---|---|
| 4,830,006 | 5/1989 | Haluska et al. .............................. | 607/4 |
| 5,184,615 | 2/1993 | Nappholz et al. . | |
| 5,350,410 | 9/1994 | Kleks et al. ............................... | 607/28 |
| 5,601,615 | 2/1997 | Markowitz et al. . | |
| 5,683,431 | 11/1997 | Wang . | |
| 5,718,720 | 2/1998 | Prutchi et al. . | |

*Primary Examiner*—William E. Kamm
*Assistant Examiner*—Carl H. Layno
*Attorney, Agent, or Firm*—Gotllieb, Rackman & Reisman, P.C.

[57] ABSTRACT

A non-invasive programming stimulation system for performing electrophysiological testing on a cardiac patient is performed using a programmer coupled to an implantable device by a communication channel. The system generates stimulating pulses for the heart and analyzes the responses to determine the pathological condition of the heart. Advantageously, before analysis, the system automatically tests for capture by the stimulating pulses to insure that the pulses do not fall into an absolute refractory period.

23 Claims, 2 Drawing Sheets

AUTOMATIC CAPTURE DETECTION DURING NON-INVASIVE PROGRAMMED STIMULATION OF A PATIENT'S HEART

BACKGROUND OF THE INVENTION

A. Field of Invention

This invention pertains to a system for performing an electrophysiological study of a patient's cardiovascular system using an implantable cardiac device coupled to an external programmer. More particularly, the present invention pertains to a system which incorporates a capture detection feature to insure that stimulation pulses delivered to the heart for a particular test have the desired effect and hence the test is not wasted.

B. Description of the Prior Art

Frequently, a clinician must perform electrophysiological studies on a patient to determine accurately the patient's pathological condition, cardiovascular characteristics and other information he may need in order to prescribe a particular therapeutic treatment for the patient. Originally, these studies were invasive because they required the surgical insertion of probes and instruments into the patient. Thus, these studies were accompanied by some risk and preferably were performed in hospitals. Therefore these studies were not only expensive but also time consuming and caused patient anxiety.

In order to avoid medical risks to the patient and hospitalization, non-invasive programmed stimulation procedures have been developed (hereinafter referred to as NIPS) which could be used to perform the required studies during a routine office visit.

Moreover, as shall be seen below, these procedures require only an implantable cardiac rhythm management device and a programmer. The implantable rhythm management device may be a pacemaker, an implantable cardioversion device or an implantable defibrillator. For the sake of brevity the device shall be referred to as an ICD.

Typical NIPS procedures consist generally of the introduction of artificial premature electrical pulses at precise intervals to the myocardium. The cardiac response to these pulses can be used for example to evaluate cardiac tachyarrhythmias, assess the functioning of the SA node, the A-V node and the HIS Purkinje system, assess the efficacy of antiarrhythmic drugs, or the ICD itself, and so on.

Basically, a typical NIPS procedure consists of three steps. First, the cardiovascular system is stimulated by the application of stimulation pulses. These pulses may be applied either externally or internally. External pulses are preferably applied to the chest wall using standard external ECG electrodes positioned on the chest of the patient. For internal stimulation, the programmer takes over the operation of the ICD and uses its pulse generator to generate the required pulses. The purpose of the procedure is to either induce or to terminate an abnormal tachyarrhythmia. The stimulator pulses may be repeated.

Prior to the start of NIPS, a train of pulses is applied to the patient's heart. This train is normally referred to as the drive train and consists typically of eight pulses spaced about 300–400 msec. This train is typically followed by 1–4 extra pulses. The interval between the drive train and the first of these extra pulses is reduced gradually until it falls in the cardiac refractory period. The interval is then increased by 10 msec.

The next step in the typical NIPS procedure is to evaluate the response of the cardiovascular system to the stimulation by recording and displaying the response. The response may be detected using either internal sensing, external sensing or both. This evaluation may occur automatically, or may be performed by the clinician himself.

The third step of the procedure is to terminate the test.

However, a problem with the existing procedures is that typically the stimulation pulses are used to overdrive the heart and to impose on it a new rhythm. If the stimulation pulses within short intervals are applied during an absolute refractory period, then these stimulations are ineffective. However, it is difficult to ascertain the occurrence of such an event until the results of the simulation pulses are evaluated. Accordingly, every stimulation train and its results must be carefully reviewed by the clinician to insure that the heart has been properly stimulated. Moreover, if a particular procedure involving stimulation results in an unstimulated heart, the test is wasted and must be repeated.

OBJECTIVES AND SUMMARY OF THE INVENTION

In view of the above-mentioned disadvantages of the existing NIPS procedures, it is an objective of the present invention to provide a system for electrophysiological testing in which ineffective stimulation is eliminated automatically.

A further objective is to provide such a system which further insures that the elements of the system are properly interconnected and properly applied to the patient.

Yet a further objective is to provide a NIPS system which can be easily adapted to provide automatic evaluation and determination of at least some of the programming parameters required to program the ICD.

Other objectives and advantages of the invention shall described in conjunction with the detailed discussion of the invention.

Briefly, a system for electrophysiological testing of a patient's cardiovascular system comprises an external programmer coupled to an ICD. The ICD includes sensors for sensing intrinsic events in the patient's heart, one or more pulse generators for generating pacing pulses and or cardioversion pulses to one or more cardiac chambers, as required, a microprocessor for generating commands to the pulse generators based on a predetermined program and the intrinsic events indicated by the sensors. The sensors and the pulse generators are coupled to internal electrodes extending into the cardiac chambers.

The programmer includes a display for displaying various waveshapes associated with the natural and artificial function of the heart as well as the various programming parameters, an input device such as a keyboard which enables the clinician to enter data and/or select various options for the operation of the programmer and a microprocessor for controlling the operation of the programmer. Optionally, one or more external ECG electrodes may also be coupled to the programmer. The programmer and the ICD device communicate through an RF communication link.

In order to perform an electrophysiological test, the programmer applies a train of stimulating pulses either directly through the external electrodes, or indirectly, through the internal electrodes associated with the cardioversion device. Importantly, the cardiac chambers are monitored immediately after the delivery of these pulses trains to determine capture if the last pacing train is not effective. If capture is not detected, the delivery of the stimulating pulses is changed and/or the clinician is alerted of a problem and potential solution to the problem.

DETAILED DESCRIPTION OF THE INVENTION

Figure 1:
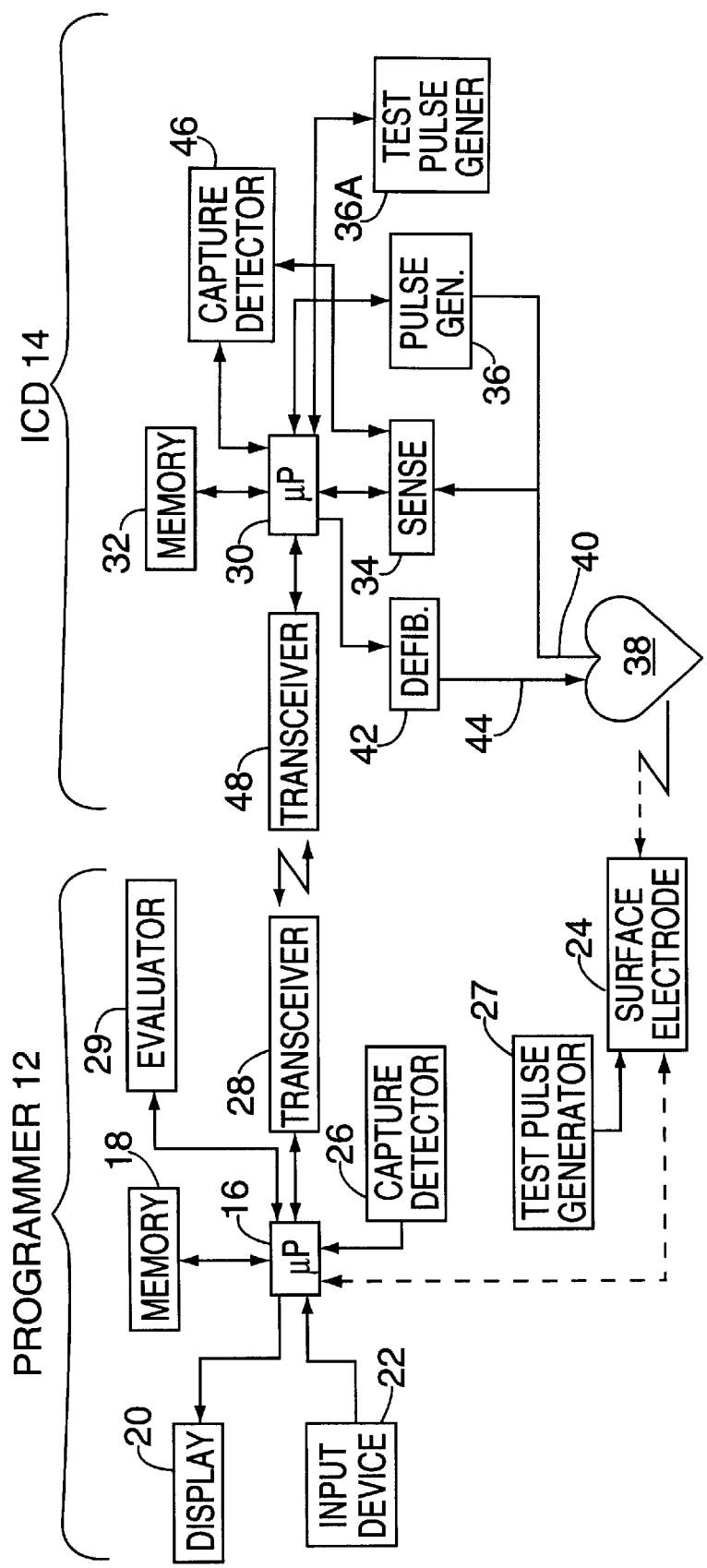
FIG. 1 shows a block diagram of a system for performing a NIPS procedure in accordance with this invention.

Referring first to FIG. 1, a system 10 for performing a NIPS procedure includes a programmer 12 and an implantable cardioversion device (ICD) 14. The programmer 12 includes a microprocessor 16, a memory 18, a display 20 and an input device 22 comprising for example a keyboard and/or a plurality of control/selection keys. The programmer may optionally be associated with a set of surface ECG electrodes 24, as well a capture detector 26. Test pulses for performing a NIPS procedure may be generated in one embodiment by a test pulse generator 27 and delivered to electrodes 24. The responses to the test pulses are analyzed by an evaluator 29.

Communication with the ICD 14 is established through a transceiver 28.

The ICD 14 includes a microprocessor 30, a memory 32, a sense circuit 34 and a pulse generator 36. The sense circuit 34 senses activity in the heart 38 of a patient through electrodes 40. Electrodes 40 are also used to apply the pulses from pulse generator 36. The ICD 14 may also include a defibrillator circuit 42 generating defibrillating shocks. These shocks are delivered to heart 38 via defibrillator electrodes 44. Pulse generator 36 may be used also to generate test pulses as described more fully below. Alternatively, a separate test pulse generator 36A may be provided.

ICD 14 may further include a capture detector 46. Communication with programmer 12 is established through a transceiver 48 which exchanges RF signals with transceiver 28 in the usual manner.

It should be understood that the capture detectors 26 and 46 and evaluator 29 may be implemented by software in microprocessors 16 and 30, however, they are shown in the Figure as discrete elements for the sake of clarity.

Normally, the ICD operates independently. In this mode, the function of the ICD 14 is to monitor the cardiac chambers of heart 38 for an abnormal arrhythmia (i.e., either for brady- or tachycardia). If bradycardia is detected, the pulse generator delivers pacing pulses to the heart on demand, or at a preselected fall back rate. In case of tachycardia, the pulse generator may deliver antitachycardia therapy by way of antitachycardia pacing pulses. Alternatively, in case of fibrillation, cardioversion, or defibrillation shocks are delivered by defibrillation shock generator 42. The programming parameters for this operation are derived either automatically or by a physician through the use of the programmer 12.

Figure 2:
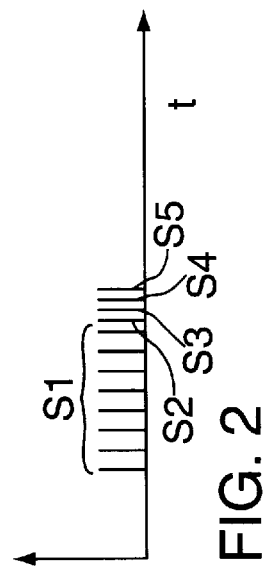
FIG. 2 shows pulse trains used for performing a NIPS procedure in accordance with this invention.

In order to perform an electrophysiological test on a patient, the two elements, programmer 12 and ICD 14 cooperate as follows. First, the physician puts the programmer 12 into a test mode. In this mode, the programmer 12 orders the ICD 14 to go into a test mode as well, during which the ICD 14 operates under the command of the programmer 12. In order to perform a test, the programmer 12 first requests the ICD 14 to deliver to the heart a train of pulses. These pulses are generated either by pulse generator 36 or by pulse generator 36A. One such train is shown in FIG. 2 as consisting of two of sets of pulses. This pulse train may be applied to either the atrium or the ventricle, dependent on what the test is designed to accomplish.

Preferably the first set is normally referred to as the drive train and may have 8–32 pulses separated by 300–400 msec intervals. The drive train is then followed by the second set of extra pulses, S2, S3, S4, S5 at intervals T. In general, the number of pulses in the second set may be 0–4. The amplitude and spacing between the extra pulses is dependent on the type of test to be performed. However, some of the pulses of the drive train may fall in the absolute post refractory period, and therefore the drive train may be ineffective. In order to overcome this problem, the present system operates as shown in FIG. 3.

Figure 3:
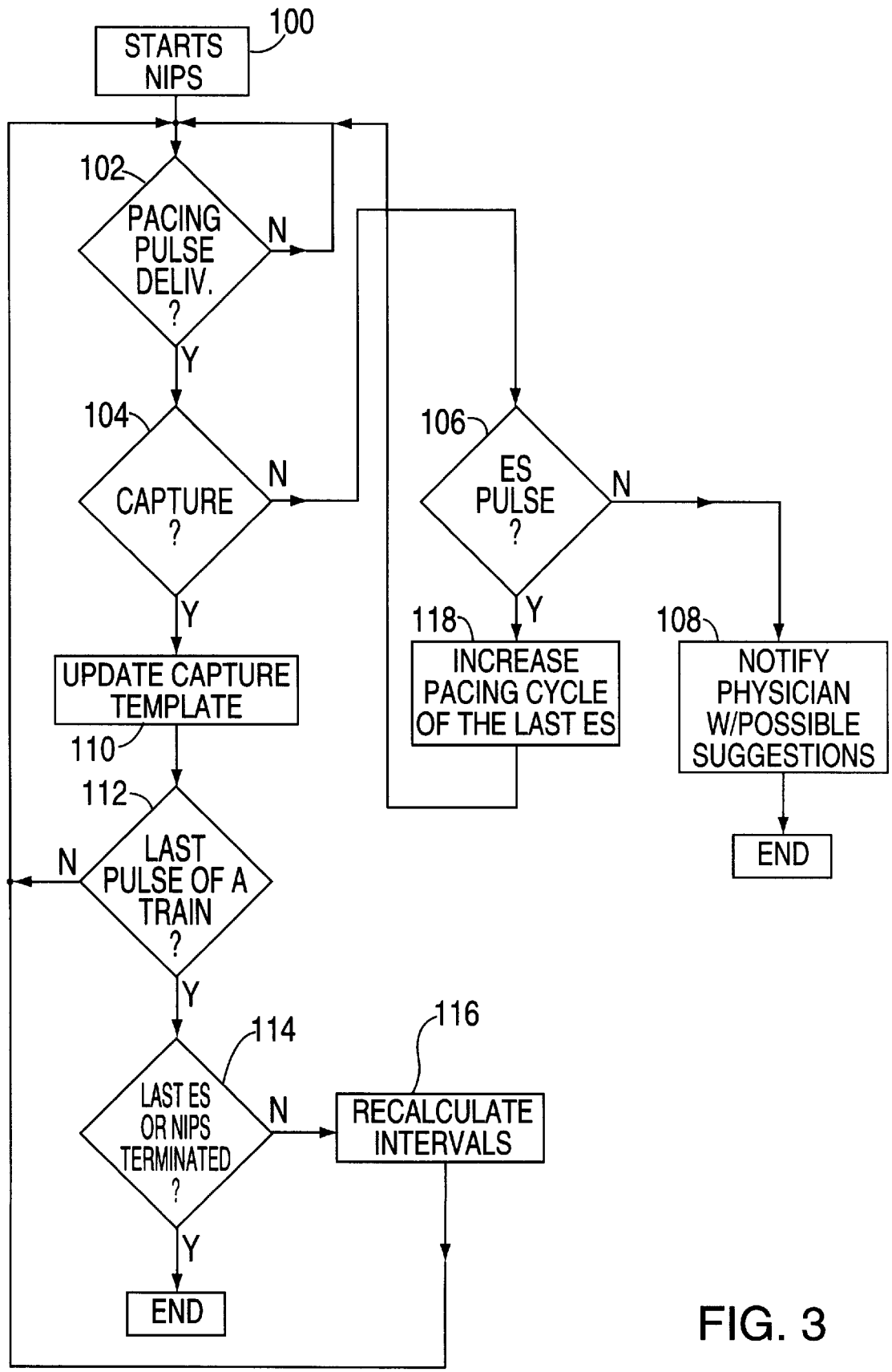
FIG. 3 shows a flow chart for performing the NIPS procedure in accordance with this invention.

In FIG. 3, the NIPS procedure is initialized in step 100. In step 102 a check is performed to detect if a pacing pulse is delivered. If it has, then in step 104 a check is performed by detector 46 (or 26) to determine if the heart was captured. If the heart was not captured then in step 106 a check is performed to determine if the last pacing pulse was an extra stimulation pulse (ES) i.e., one of the pulses S2–S5. If not then in step 108, the programmer 12 notifies the physician that capture has not been accomplished for the drive train together (optionally) with a possible suggestion on how to change the pacing pulses or electrode positioning to insure capture.

For the purposes of this description it is assumed that capture is detected from morphological analysis or using the Paced Depolarization Integral (PDI) (as described in U.S. Pat. No. 5,184,615) and that a template of a sensed signal indicative of capture has been previously stored in memory 32 or 18 (i.e., prior to the beginning of the NIPS procedure).

If in step 104 capture is detected then in step 110, the capture template is updated. In step 112 a check is performed to determine if the latest pacing pulse was the last SI pulse of the drive train. If it was not then the NIPS procedure continues. If it is the last pulse then in step 114 a check is performed to determine if (a) the last pacing pulse in a pulse train and all required ES have been delivered, or (b) if the physician requests that the NIPS procedure be terminated. If either of these conditions is met then the NIPS procedure is then completed. If these conditions are not met, the pacing interval for the next pacing pulse train is calculated in step 116. For example, the interval for the current extra stimulus may be decreased (e.g.by 10 ms) or the next extra stimulus is added. The procedure then returns to step 102.

Getting back to step 106, if an extra stimulation pulse has been delivered but the pulse did not result in capture, then in step 118 the interval of the current extra stimulation pulse is increased and the NIPS procedure returns to step 102 with the ESI calculated in step 118 being used only for the last extra stimulus. The ESI may be increased by adding a 10 ms margin.

The invention has been described in conjunction with a NIPS procedure in which a drive train and extra pulses are used for stimulation, as discussed above. However, other NIPS procedures may use a burst of 30 stimulation pulses with no extra pulses. Alternatively, a graduated pulse train may be used in which the intervals are gradually decreased and then increased. The subject invention is equally applicable to these types of pulse trains as well.

Although the invention has been described with reference to particular embodiments, it is to be understood that such embodiments are merely illustrative of the application of the principles of the invention. Accordingly, the embodiments described in particular should be considered exemplary, not limiting, with respect to the following claims.

I claim:

1. A cardiac non-invasive programmed stimulation system for performing an electrophysiological test on a patient comprising:
   a. an implantable device having
      (i) a sense circuit for sensing electrical activity in said patient's heart, said sense circuit generating a corresponding sense signal;
      (ii) a pace generator for generating pulses for the heart in response to commands;
      (iii) a controller for receiving said sense signals and for generating said commands in accordance with a program defined by programming information; and
      (iv) an implant transceiver for receiving said programming information for said controller;
   B. An external programmer having
      (i) an input device for receiving instructions;
      (ii) a controller for receiving said instructions and generating said programming information, said programming information defining for said implantable device a test mode of operation;
   C. a test pulse generator for selectively generating test pulses for said heart while said implantable device is in said test mode, including a first set of test pulses and a second set of test pulses; and;
   D. a capture detector for automatically detecting when said test pulses of said second set of test pulses capture said heart wherein said test pulse generator is coupled to said capture detector to adjust a characteristic of said second pulses when said capture detector does not detect capture by said second set of test pulses.

2. The system of claim 1 wherein said implantable device has an implantable housing and said capture detector is disposed in said implantable housing.

3. The system of claim 1 wherein said programmer has a programmer housing and said capture detector is disposed in said programmer housing.

4. The system of claim 1 wherein said implantable device has an implantable housing and said test pulse generator is disposed in said implantable housing.

5. The system of claim 1 wherein said programmer has a programmer housing and said test pulse generator is disposed in said programmer housing.

6. The system of claim 1 wherein said second set of pulses have a pulse interval and wherein said test generator changes said pulse interval when said capture detector indicates that some pulses of said second set did not result in capture.

7. The system of claim 1 wherein said test generator does not generate said second set of pulses if said capture detector indicates that said first set of pulses did not result in capture.

8. A NIPS system for evaluating the electrophysiological characteristics of a patient, said system comprising:
   a test generator for generating selectively test pulses, including a first set of test pulses and a second set of test pulses;
   electrodes coupled to said test generator and arranged to deliver said test pulses to the patient's heart;
   a sense circuit for sensing responses from said heart corresponding to said test pulses;
   a capture detector coupled to said sense circuit to detect when said heart is captured by said test pulses; and
   an evaluator for evaluating said responses once said capture is indicated by said capture detector, wherein said test generator is adapted to generate said second set of pulses when said capture detector indicates that at least some pulses of said first set result in capture;
   said test generator being further adapted to modify a characteristic of said second set of pulses if said capture detector indicates that at least some pulses of said second set do not result in capture.

9. The system of claim 8 further comprising a programmer and an implantable device.

10. The system of claim 9 wherein said programmer includes a programmer housing and said test generator is disposed in said programmer housing.

11. The system of claim 8 wherein said implantable device includes an implantable housing and said test generator is disposed in said implantable housing.

12. The system of claim 8 wherein said electrodes comprise implanted electrodes.

13. The system of claim 8 wherein said electrodes comprise surface electrodes.

14. The system of claim 8 further comprising an implantable device having a first and a second mode of operation, wherein said sense circuit is disposed in said implantable device and generates sense signals.

15. The system of claim 14 wherein said implantable device in said first mode operates independently to monitor said heart through said sense circuit, said implant further including an implantable housing and an implant pulse generator disposed in said implant housing and is responsive to said sense signals to generate therapeutic pulses.

16. The system of claim 15 wherein said test generator is disposed in said implantable housing and comprises said implant pulse generator.

17. A method of non-invasive programmed stimulation of a patient's heart using a programmer and an associated implantable device in communication therewith, comprising the steps of:
   generating a first train of pulses by one of said programmer and said implantable device;
   testing if any pulses of said first train of pulses resulted in a capture of said heart;
   terminating said testing if none of said pulses of said first train results in said capture: and
   if said capture is present, evaluating the responses of the heart to said train of pulses.

18. The method of claim 17 further comprising:
   generating a second train of second pulses if at least one of said first pulses results in capture;
   testing if any of said second pulses result in capture; and
   if at least some of the second pulses do not result in capture, then adjusting a characteristic of said second pulses.

19. The method of claim 18 further comprising adjusting an interval between said second pulses.

20. The method of claim 17 further comprising generating said train in said programmer.

21. The method of claim 17 further comprising generating said train in said implantable device.

22. A cardiac non-invasive programmed stimulation system for performing an electrophysiological test on a patient comprising:
   a. an implantable device having
      (i) a sense circuit for sensing electrical activity in said patient's heart, said sense circuit generating a corresponding sense signal;
      (ii) a pace generator for generating pulses for the heart in response to commands;

(iii) a controller for receiving said sense signals and for generating said commands in accordance with a program defined by programming information; and (iv) an implant transceiver for receiving said programming information for said controller;

B. An external programmer having a programmer housing with:

(i) an input device for receiving instructions;

(ii) a controller for receiving said instructions and generating said programming information, said programming information defining for said implantable device a test mode of operation;

C. a test pulse generator for generating test pulses for said heart while said implantable device is in said test mode;

D. a capture detector for automatically detecting when said test pulses capture said heart, said capture detector being disposed in said programmer housing; and E. a test evaluator for evaluating responses from said heart to said test pulses in the event of capture.

23. A cardiac non-invasive programmed stimulation system for performing an electrophysiological test on a patient comprising:

a. an implantable device having (i) a sense circuit for sensing electrical activity in said patient's heart, said sense circuit generating a corresponding sense signal;

(ii) a pace generator for generating pulses for the heart in response to commands;

(iii) a controller for receiving said sense signals and for generating said commands in accordance with a program defined by programming information; and (iv) an implant transceiver for receiving said programming information for said controller;

B. An external programmer having a programmer housing with:

(i) an input device for receiving instructions;

(ii) a controller for receiving said instructions and generating said programming information, said programming information defining for said implantable device a test mode of operation;

C. a test pulse generator for generating test pulses for said heart while said implantable device is in said test mode, said test pulse generator being disposed in said programmer housing;

D. a capture detector for automatically detecting when said test pulses capture said heart; and E. a test evaluator for evaluating responses from said heart to said test pulses in the event of capture.

\* \* \* \* \*